(12) United States Patent
Pas

(10) Patent No.: US 9,255,701 B2
(45) Date of Patent: Feb. 9, 2016

(54) LIGHTING DEVICE, AND LIGHTING SYSTEM

(75) Inventor: Kobbe Olaf Pas, Haarlem (NL)

(73) Assignee: Nobel Groep B.V., Haarlem (NL)

( * ) Notice: Subject to any disclaimer, the term of this patent is extended or adjusted under 35 U.S.C. 154(b) by 157 days.

(21) Appl. No.: 14/241,670

(22) PCT Filed: Aug. 29, 2012

(86) PCT No.: PCT/NL2012/050590
§ 371 (c)(1),
(2), (4) Date: May 21, 2014

(87) PCT Pub. No.: WO2013/032326
PCT Pub. Date: Mar. 7, 2013

(65) Prior Publication Data
US 2014/0321120 A1   Oct. 30, 2014

(30) Foreign Application Priority Data
Aug. 29, 2011   (NL) ..................................... 2007316

(51) Int. Cl.
| | |
|---|---|
| F21V 29/00 | (2015.01) |
| F21V 23/00 | (2015.01) |
| F21V 33/00 | (2006.01) |
| A61L 9/03 | (2006.01) |
| F21V 29/83 | (2015.01) |
| F21Y 101/02 | (2006.01) |
| F21Y 111/00 | (2006.01) |

(52) U.S. Cl.
CPC ............... *F21V 29/004* (2013.01); *A61L 9/03* (2013.01); *F21V 23/009* (2013.01); *F21V 29/83* (2015.01); *F21V 33/00* (2013.01); *A61L 2209/12* (2013.01); *F21Y 2101/02* (2013.01); *F21Y 2111/007* (2013.01)

(58) Field of Classification Search
CPC ..... A61L 9/03; A61L 2209/12; F21V 23/009; F21V 29/83; F21V 29/004; F21V 33/00; F21Y 2101/02; F21Y 2111/007
See application file for complete search history.

(56) References Cited

U.S. PATENT DOCUMENTS 7,144,135 B2 * 12/2006 Martin .................... F21K 9/137
362/294
2009/0073688 A1   3/2009   Patrick

FOREIGN PATENT DOCUMENTS

| EP | 2 236 917 A1 | 10/2010 |
|---|---|---|
| WO | WO 2012/007403 A1 | 1/2012 |

* cited by examiner

*Primary Examiner* — Stephen F Husar
(74) *Attorney, Agent, or Firm* — Dickstein Shapiro LLP

(57) ABSTRACT

A lighting device (100) has a support structure having lighting elements (422) arranged thereon. The support structure has an internal cooling duct having a duct wall. At least a part of duct wall is in thermal contact with the lighting elements. The cooling duct is configured to allow a natural air flow absorbing heat generated by the lighting elements from the duct wall. The cooling duct extends through the support structure from a first opening having a first cross-sectional area to a second opening having a second cross-sectional area. The cooling duct contains a filler body (412) having a substantially bi-conical shape. The filler body and the duct wall form a cooling duct portion with a third cross-sectional area greater than the first cross-sectional area and/or the second cross-sectional area. The lighting device is part of a lighting system. The system comprises a control unit (700) coupled to the lighting device.

20 Claims, 11 Drawing Sheets

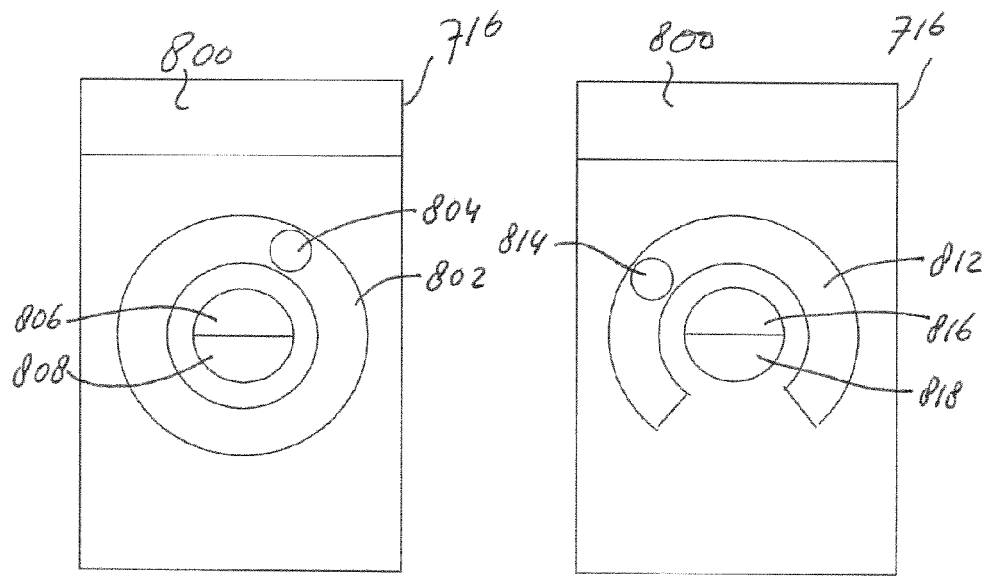
FIG. 14       FIG. 15
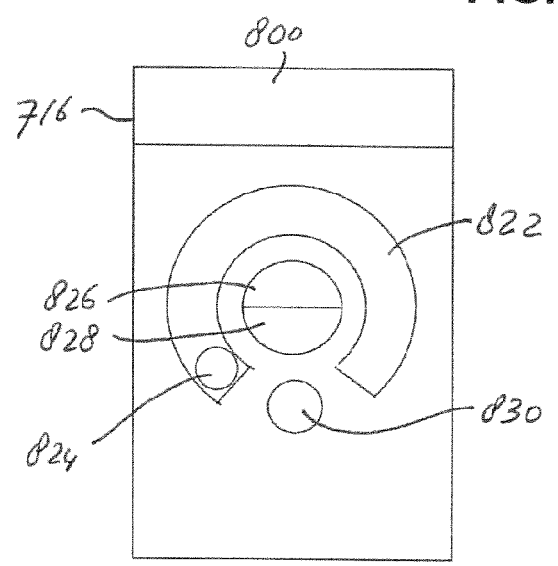
FIG. 16

LIGHTING DEVICE, AND LIGHTING SYSTEM

FIELD OF THE INVENTION

The invention relates to the field of lighting, and more specifically to a lighting device and a lighting system comprising the lighting device. More in detail, the present invention relates to cooling and control of a lighting device.

BACKGROUND OF THE INVENTION

In a lighting device, primary energy—usually electrical energy—supplied thereto is converted into light, i.e. radiation having a wavelength in the visible range. Although the efficiency of the energy conversion from the primary energy into light energy may be quite high, still a portion of the primary energy will be converted into heat energy when generating light energy. The heat that is generated in the lighting device needs to be discharged to avoid temperatures in the lighting device to rise beyond acceptable limits.

Reference US 2009/0073688 discloses a light fixture including a member having a substantially frusto-conical shape. Light emitting diodes, LEDs, are disposed on the member. A channel in the member is configured to transfer heat generated by the LEDs through convection.

Reference US 2010/0314985 discloses a LED light bulb having a hollow LED support/heat sink with fins extending internally. Heat generated by the LEDs is conducted through the heat sink fins and is removed by a convectively driven air flow that flows through the LED support/heat sink.

For higher lighting outputs and/or lower construction volumes of the lighting device, the reference explains that passive cooling may be insufficient, and active cooling should be applied, e.g. by application of a cooling fan drawing air through the LED support, or by application of a corona discharge air pump to stimulate air flow through the LED support.

However, an additional component like a cooling fan requires additional space in the lighting device, requires energy, and may involve a device having moving parts which are susceptible to wear and produce noise.

SUMMARY OF THE INVENTION

It would be desirable to provide a lighting device having a relatively high lighting output in a relatively low construction volume. It would also be desirable to provide a lighting device having an improved cooling capacity at a convectively driven air flow.

To better address one or more of these concerns, in a first aspect of the invention a lighting device is provided that comprises a support structure having lighting elements arranged thereon. The support structure comprises an internal cooling duct having a duct wall, at least a part of duct wall being in thermal contact with the lighting elements. The cooling duct is configured to allow a natural air flow absorbing heat generated by the lighting elements from the duct wall. The cooling duct extends through the support structure from a first opening having a first cross-sectional area to a second opening having a second cross-sectional area. The cooling duct contains a filler body, the filler body and the cooling duct in combination forming a cooling duct portion having a third cross-sectional area larger than the first cross-sectional area and/or the second cross-sectional area. The filler body has a substantially bi-conical shape.

At the cooling duct portion having the enlarged third cross-sectional area, a space is created that may be regarded as a buffer space. In this buffer space, a flow velocity of the air in the cooling duct may decrease considerably compared to its velocity at the first or second cross-sectional area, whereby the air is allowed more time to absorb heat from the cooling duct wall than in an embodiment which would not have such buffer space having the enlarged third cross-sectional area. This increased amount of absorbed heat leads to an increase in pressure in the air in the buffer space, and consequently an increased thermally driven air flow in the cooling duct develops.

When a filler body is used to create the third cross-sectional area, the air in the cooling duct is forced to travel a longer distance along the cooling duct wall than in an embodiment which would not have a filler body. This in turn may lead to a further increased amount of absorbed heat in the buffer space.

In some embodiments, the duct wall may be provided with inwardly extending fins which conduct heat input to the duct wall into the cooling duct where it may be transferred to the air flowing in the cooling duct more effectively. The fins may be integrally formed with the duct wall, and extend substantially in the air flow direction.

In some embodiments, the filler body may be arranged at a distance from the duct wall, where the filler body may be connected to the duct wall by support rods or similar structures which do not substantially obstruct an air flow in the cooling duct.

In an embodiment, the filler body is arranged centrally in the cooling duct, allowing the air to flow along the entire inner surface of the cooling duct. The filler body of the lighting device having a substantially bi-conical shape forces the air in the cooling duct to flow along the inner surface of the cooling duct. The filler body of the lighting device having a substantially bi-conical shape allows to construct a lighting device with a sphere-like form.

In some embodiments, the filler body my be mounted on the duct wall, or may be formed as an inward protrusion of the duct wall.

In an embodiment, at least a part of the duct wall opposite the filler body is in thermal contact with the lighting elements. Here, heat produced by the lighting elements will be radiated at the buffer space where it can be absorbed efficiently by the air flow in the cooling duct.

In an embodiment, in use of the lighting device, the second opening is at a higher vertical level than the first opening. An air flow in the cooling duct will flow from the first opening to the second opening.

In some embodiments, in use of the lighting device, the first opening is at a bottom side of the support structure and/or the second opening is at a top side of the support structure, to provide an optimum air flow in the cooling duct.

In an embodiment, the cooling duct comprises two substantially frusto-conical parts having bases connected to one another. The frusto-conical parts may provide an increase of the cross-sectional area of the cooling duct, as desired for an increased heat transfer from the duct wall to the air in the cooling duct. As an example, such an embodiment may be combined with a filler body having a substantially bi-conical shape mounted centrally in the cooling duct.

In an embodiment, the lighting elements are mounted on an outer surface of the frusto-conical parts to provide a lighting device which may radiate light in a broad range of directions, or which may radiate light in all directions.

In an embodiment, the frusto-conical parts are multi-faceted to define mounting planes for the lighting elements to facilitate the production of the lighting device.

In an embodiment, the lighting elements comprise light emitting diodes, LEDs. A plurality of LEDs may be distributed on the support structure in thermal contact with the cooling duct wall to provide a desired intensity and color of light, while at the same time providing an efficient cooling of the lighting elements. A lighting element may comprise an electrical circuit element generating heat, and not producing light.

As an aesthetically appealing structure, the support structure comprises a light-transmitting sphere-shaped enclosure.

In an embodiment, the lighting device may comprise a scent agent diffuser arranged in the cooling duct or arranged to be in the air flow downstream of the cooling duct. With the natural air flow generated in the lighting device during use thereof, the flowing air may be used to diffuse a scent agent in a space surrounding the lighting device.

In an embodiment, the scent agent diffuser of the lighting device has a surface arranged to be in contact with the air flow. The surface may be shaped such that a sufficient surface area is available to allow the flowing air to absorb scent agent for distribution into the environment.

In an embodiment, the lighting device may comprise a rotor configured to be driven by the air flow. In some embodiments, the rotor may be connected to a toy to move the toy during use of the lighting device. In some embodiments, the rotor may be connected to a generator generating electrical energy which may be supplied to the lighting elements to reduce their power consumption from another source, such as a mains voltage.

In a second aspect of the present invention, a lighting system comprising the lighting device of the invention is provided. The lighting system further comprises: a control unit coupled to the lighting device, the control unit being configured to receive control data and to cause the lighting device to operate based on the control data; and a user device configured to generate input to an application program configured to generate the control data based on the input, and to transmit the control data to the control unit. The user device, which may e.g. be a computer or a smartphone, allows for a flexible and comprehensive control of the lighting device, where the control data may be transmitted through wires, or wirelessly, to the control unit of the lighting device. It is noted that the lighting device of the lighting system may be a lighting device according to the present invention, but could also be another lighting device controllable through a control unit.

In an embodiment of the lighting system, the user device comprises a touch screen, and the input to the application program is generated by the user manipulating the touch screen. A display of the touch screen may show visual elements or items which may be touched and/or moved by a user to enable a predetermined function to be performed, such as setting a color of the light emitted by the lighting device or a part thereof, setting a saturation of the light emitted by the lighting device or a part thereof, and/or setting a dimming level of the light emitted by the lighting device or a part thereof.

In an embodiment of the lighting system, the user device comprises an acceleration sensor, and the input to the application program is generated by the user moving, in particular shaking, the user device. Control data generated by moving the user device may perform a function of selecting or storing a particular light setting of the lighting device or a part thereof.

In an embodiment of the lighting system, the user device comprises a microphone, and the input to the application program is generated by the user providing a sound or speech to the microphone. Control data generated by providing a sound, like a noise of blowing at the microphone, or speech, like specific words, to the microphone may perform a function of dimming or selecting or storing a particular light setting of the lighting device or part thereof.

In a further aspect of the present invention, a lighting system comprising the lighting device of the invention is provided, wherein the lighting system further comprises: a control unit coupled to the lighting device, the control unit being configured to receive status data from the lighting device, and to transmit the status data to an application program. Status data may relate to a temperature value of a part of the lighting device, as measured by a temperature sensor in the lighting device. The temperature value may e.g. indicate that the cooling duct is blocked by showing a high temperature. Maximum temperature values may be stored in the application program, or the control unit, or the lighting device.

In an embodiment of the lighting system, the transmission of the control data or the status data is through a network, such as the Internet or a local network. This implies that any place where a network connection, nowadays often referred to as a wifi connection, is available, data may be exchanged between an application program and the control unit of the lighting device.

In a further aspect of the invention, a lighting system comprising the lighting device of the invention is provided. The lighting system comprises an orientation sensor for sensing an orientation of the lighting device, the orientation sensor configured to output an orientation signal. The lighting system further comprises a control module for receiving the orientation signal, and for controlling at least one of the lighting elements depending on the orientation sensed by the orientation sensor. In some embodiments, a vertical orientation may be sensed, the orientation signal providing information as to which part of the lighting device faces downwardly (and, accordingly, which part of the lighting device faces upwardly). With this information, some lighting elements having known positions on the lighting device may be controlled to radiate a particular intensity and/or color of light.

These and other aspects of the invention will be more readily appreciated as the same becomes better understood by reference to the following detailed description and considered in connection with the accompanying drawings in which like reference symbols designate like parts.

BRIEF DESCRIPTION OF THE DRAWINGS

FIGS. 14, 15 and 16 schematically depict different displays of a control device of a lighting system according to FIG. 12 or FIG. 13.

DETAILED DESCRIPTION OF EMBODIMENTS

Within the context of the invention as disclosed herein, the indications 'top', 'upper', 'bottom' and 'lower' refer to an orientation of a lighting device in use thereof.

Figure 1:
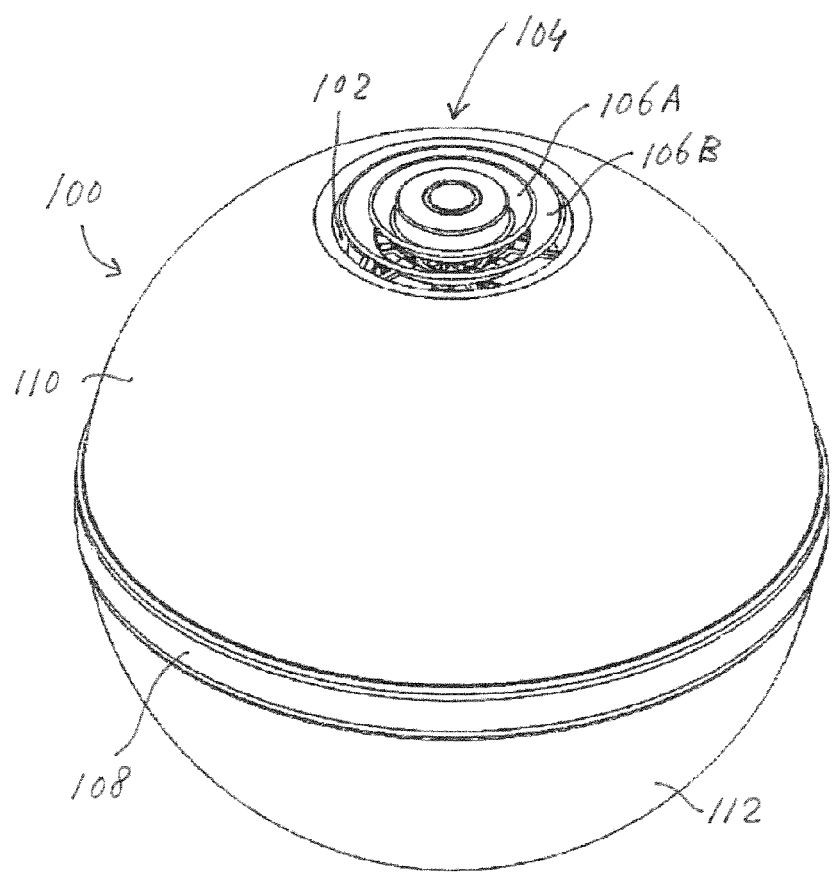
FIG. 1 depicts a perspective view of an embodiment of a lighting device according to the present invention.
Figure 2:
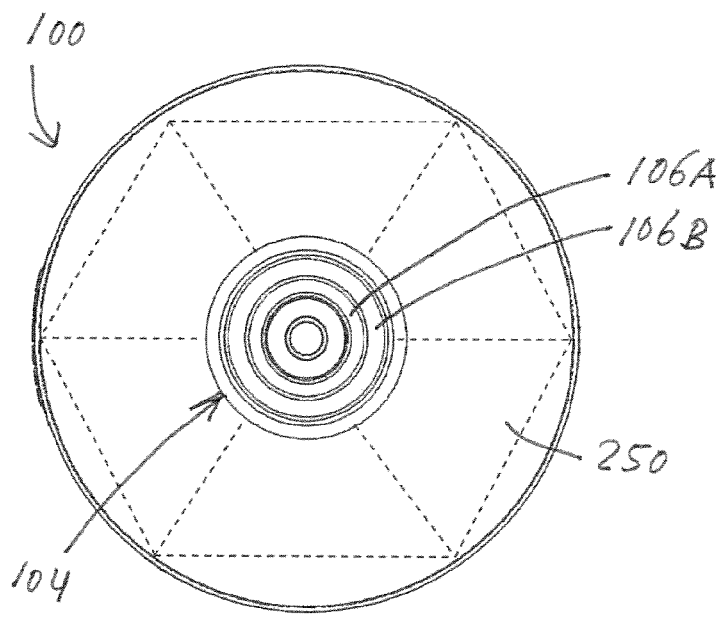
FIG. 2 depicts an elevated view of the embodiment of the lighting device of FIG. 1.
Figure 3:
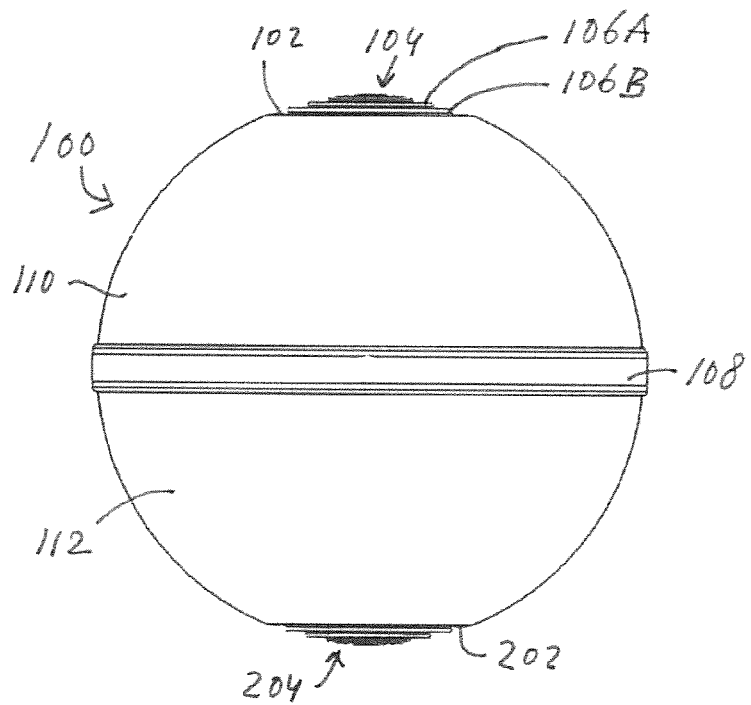
FIG. 3 depicts a side view of the embodiment of the lighting device of FIG. 1.

FIGS. 1, 2 and 3 depict a lighting device 100 having a generally spherical outer surface. At a top side of the lighting device 100, a top opening 102 is provided having a top air flow guiding member 104 placed therein. The top air flow guiding member 104 comprises one or more (in the embodiment shown in FIG. 1: two) tapering, ring-shaped fins 106A, 106B. At a bottom side of the lighting device 100, a bottom opening 202 similar to the top opening 102, and a bottom air flow guiding member 204 similar to the top air flow guiding member 104 are provided, oppositely to the top opening 102 and top air flow guiding member 104 at the top side of the lighting device 100. The top opening 102 at the top side of the lighting device 100 is connected to the bottom opening 202 at the bottom side of the lighting device 100 by a duct, as will be explained in more detail below by reference to FIG. 4. A ring 108 extending around the spherical surface of the lighting device 100 covers a partition area where an upper half sphere 110 joins a lower half sphere 112.

Figure 4:
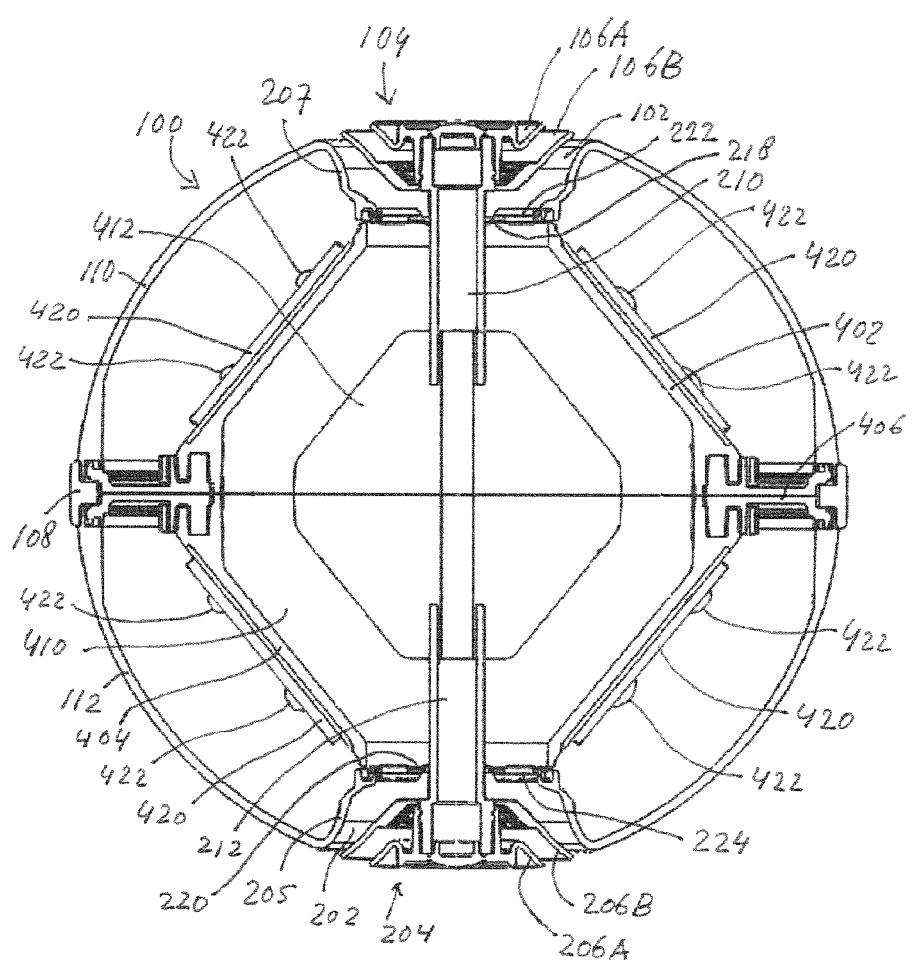
FIG. 4 depicts a cross-sectional view of the embodiment of the lighting device of FIG. 1.

FIG. 4 illustrates an embodiment of a support structure of the lighting device 100. The upper half sphere 110 has its top opening 102 adjoining a tapering duct part 207 extending inwardly. Similarly, the lower half sphere 112 has its bottom opening 202 adjoining a tapering duct part 205 extending inwardly.

In the opening 102, and further extending in the duct part 207, ring-shaped fins 106A, 106B are arranged centrally. Likewise, in the opening 202, and further extending in the duct part 205, ring-shaped fins 206A, 206B are arranged centrally. The fins 106A, 106B, and 206A, 206B are supported on respective tubular members 210, 212, while these tubular members 210, 212 each are supported by rings 218, 220, respectively, connected by radially extending spokes 222, 224, respectively, to an end of the duct part 207, 205, respectively.

In other embodiments, top air flow guiding member 104 and/or bottom air flow guiding member 204 may be omitted. Further, in other embodiments the duct parts 205, 207 may have different configurations, such as straight instead of tapered.

Between the duct parts 205 and 207, a duct part formed by two substantially frusto-conical parts 402, 404 having their bases connected to one another extends. In combination, the duct parts 205, the frusto-conical parts 402, 404, and the duct part 207 form a cooling duct 410 in the lighting device 100. The frusto-conical parts 402, 404 are interconnected by a profiled ring 406 which further connects the parts 402, 404 to the half spheres 110, 112.

In the cooling duct 410, a filler body 412 is arranged centrally. The filler body 412 has a substantially bi-conical shape. The filler body 412 is mounted on the tubular members 210, 212 which extend into the filler body 412.

At the outer surface of the frusto-conical parts 402, 404, i.e. at the outer surface of the cooling duct 410, heat generating electrical circuitry 420 (optional) and lighting elements 422, such as LEDs, may be mounted. A heat transfer between lighting elements 422 and the frusto-conical parts 402, 404—which form part of the duct wall—may be ensured by a thermal contact between the elements 422 and the parts 402, 404. The circuitry 420 may comprise control and supply circuitry for the lighting elements 422. The arrangement of the LEDs, when distributed over the outer surface of the frusto-conical parts 402, 404, allows the lighting device 100 to radiate light in virtually all directions. As illustrated in an embodiment by dashed lines in FIG. 2, the frusto-conical parts 402, 404 may be multi-faceted to define mounting planes for the circuitry 420 and/or the other lighting elements 422. In the embodiment of FIG. 2, each frusto-conical part 402, 404 has six facets or planes 250.

The cooling duct 410, at the location of the ring 220, has a first cross-sectional area A. At the location of the ring 218, the cooling duct 410 has a second cross-sectional area B. Between the locations of the rings 218, 220, the cooling duct 410 has a third cross-sectional area C. In the exemplary embodiment illustrated, area C is larger than area A or area B, and area A is equal to area B.

It is noted that the tubular member 210 may be used for connecting a hanger or other hanging structure (not shown in detail), and that the tubular member 212 may be used for connecting a stand or foot or other supporting structure (not shown in detail) for the lighting device 100.

As an illustration of the cooling effect by the cooling duct 410 in the lighting device 100, the following explained by reference to FIG. 4. At the location of opening 202, air from the environment of the lighting device 100 may enter the cooling duct 410 through an substantially ring-shaped cross-section having a first cross-sectional area A. Between opening 202 and a location at the level of profiled ring 406, air in the cooling duct absorbs heat generated by lighting elements 422 mounted around the corresponding cooling duct part, and the ring-shaped cross-sectional area of the cooling duct increases to become a ring-shaped third cross-sectional area C at the location of the ring 406. At the same time, the filler body 412 limits the cross-sectional area C, and forces the air to flow along the cooling duct wall to increase the heat absorption there. In embodiments, the area C may be at least twice the area A. In further embodiments, the area C may be at least four times the area A. The increase of the cross-sectional area of the cooling duct from opening 202 to the location of the ring 406 results in a decrease of the air flow velocity, providing increased time for the air to absorb heat from the cooling duct wall. At the same time, the filler body 412 forces the air to flow along the cooling duct wall, thereby increasing the absorption of heat by the air. As a consequence, at the location of the opening 102, where the cooling duct 410 has a substantially ring-shaped cross-sectional area B, a relatively high pressure, and consequently also a relatively high pressure and a relatively high mass flow in the cooling duct prevail, when e.g. compared to an embodiment having a straight cooling duct having the same cross-sectional area A along its length, and being subjected to the same heat input at its cooling duct wall.

It is noted that in case of multi-faceted frusto-conical parts 402, 404, as illustrated in FIG. 2, the circumference of the openings 102, 202 may be hexagonally shaped.

Figure 5:
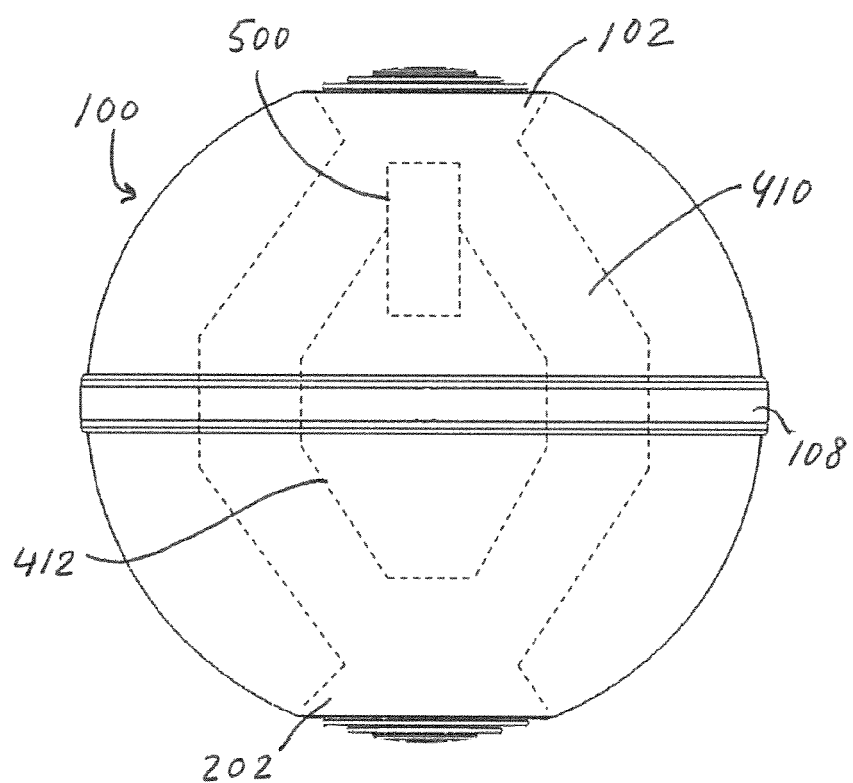
FIG. 5 illustrates a use of a scent agent diffuser or a rotor using an air flow generated in the lighting device.

FIG. 5 illustrates the lighting device 100 having a cooling duct 410 as exemplified in FIG. 4 (indicated by a dashed contour), and comprising the filler body 412. In the lighting device 100, e.g. mounted in an upper or lower part thereof, mounted on the filler body 412, or otherwise arranged in the cooling duct 410 or downstream of the cooling duct 410, a scent agent diffuser or rotating device, generally indicated by reference numeral 500, may be provided such that the air flow in or from the cooling duct 410 contacts the scent agent diffuser or rotating device 500. The scent agent diffuser or rotating device 500 may be mounted in or on the lighting device 100 through a screwed connection, where the scent agent diffuser or rotating device 500 has a threaded portion configured to engage a corresponding threaded portion of the lighting device 100. Alternatively or additionally, the scent agent diffuser or rotating device 500 may be mounted in or on the lighting device 100 through a friction connection, where the scent agent diffuser or rotating device 500 has a portion configured to frictionally engage a corresponding portion of the lighting device 100. Alternatively, or additionally, the scent agent diffuser or rotating device 500 may be mounted in or on the lighting device 100 through a bayonet or snap connection, where the scent agent diffuser or rotating device 500 has a portion configured to bayonet-connect or snap-connect to a corresponding portion of the lighting device 100. Alternatively or additionally, the scent agent diffuser or rotating device 500 may be mounted in or on the lighting device 100 through a glued connection, where the scent agent diffuser or rotating device 500 has a portion configured to be glued to a corresponding portion of the lighting device 100. Alternatively or additionally, the scent agent diffuser or rotating device 500 may be mounted in or on the lighting device 100 through a magnetic connection, where the scent agent diffuser or rotating device 500 has a portion configured to adhere to a corresponding portion of the lighting device 100 through magnetic force. Hereto, said part of one of the scent agent diffuser or rotating device 500 may be provided with a permanent magnet, and said part of the other one of the scent agent diffuser or rotating device 500 may be provided with a permanent magnet, or be provided with a magnetizable material.

In case of a scent agent diffuser 500, an air flow in the cooling duct 410, generated by heat which in turn is generated by circuitry 420 and lighting elements 422 in operation, may take evaporated scent agent along, and spread it into the environment of the lighting device 100 while flowing out of the cooling duct 410 through opening 102.

In case of a rotor 500 (such as a turbine), an air flow in the cooling duct 410 may set the rotor 500 into motion. In turn, the rotor 500 may drive e.g. a generator to generator power to be used e.g. for partly powering the lighting elements 422. The rotor 500 may also drive a toy (not shown in detail) coupled to the rotor 500, to move (e.g. rotate) the toy by the air flowing in the cooling duct 410.

Figure 6:
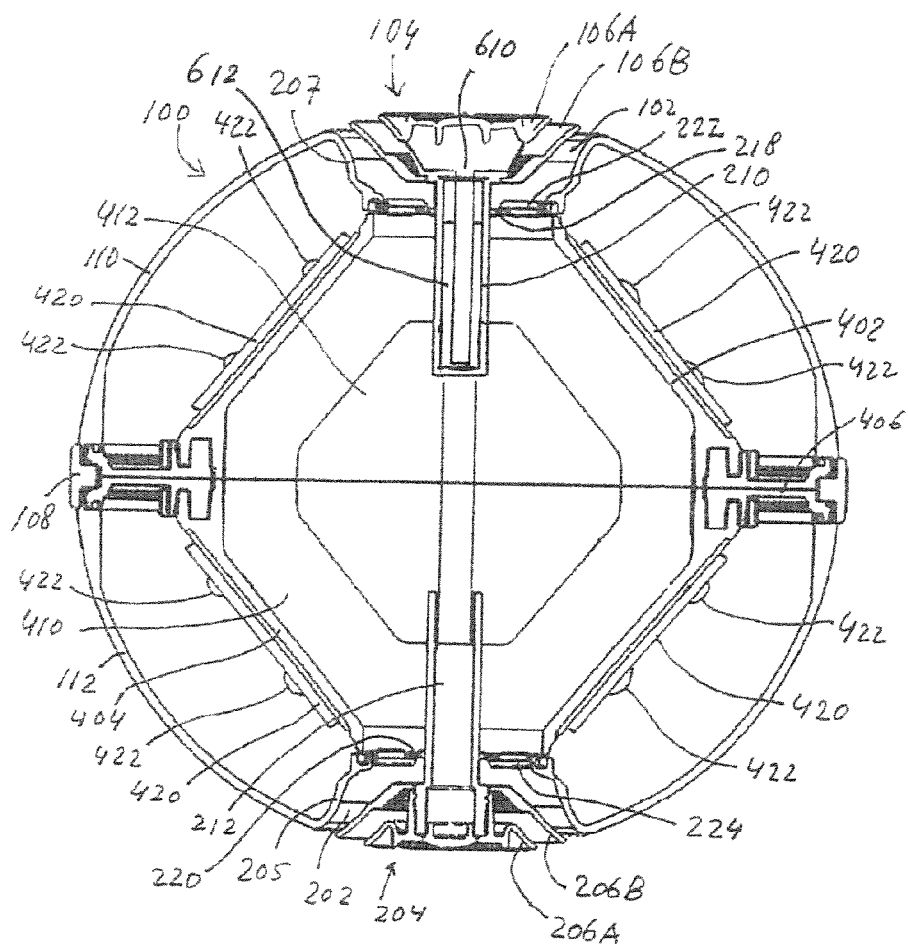
FIG. 6 depicts a cross-sectional view of a further embodiment of a lighting device according to the present invention, including a scent agent diffuser.
Figure 7:
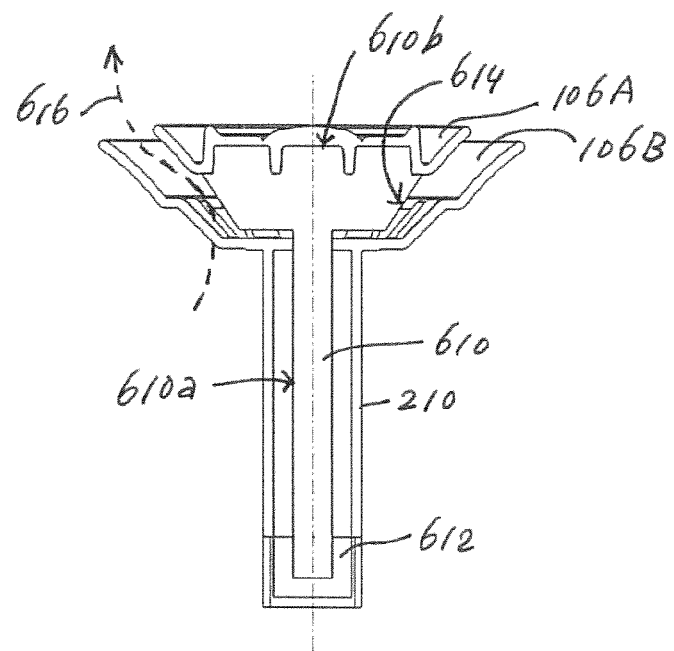
FIG. 7 depicts a cross-sectional view of a scent agent diffuser of the embodiment of the lighting device of FIG. 6.
Figure 8:
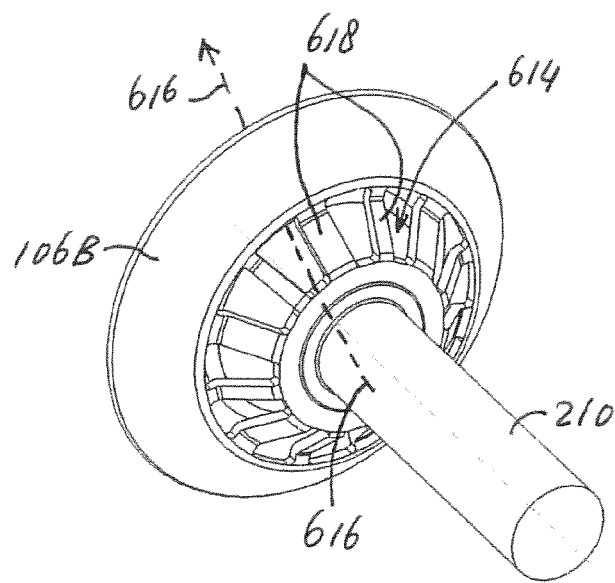
FIG. 8 depicts a perspective view of the scent agent diffuser of FIG. 7.

FIGS. 6, 7 and 8 depict a scent agent diffuser 610 configured to be accommodated in an embodiment of the lighting device 100 as illustrated by FIG. 4. In particular, FIG. 6 illustrates the scent agent diffuser 610 being mounted at the top of the lighting device 100. As shown more in detail in FIG. 7, the scent agent diffuser 610 comprises a body having an elongated, cylindrical portion 610a and a substantially frusto-conical shaped portion 610b, which portions 610a, 610b may be separately, or integrally formed. The portion 610a contacts a liquid or gel 612 carrying a scent agent. The liquid or gel 612 is taken up by the scent agent diffuser 610 material, which may be sponge-like or similar, such that at least the scent agent is available in the portion 610b at a conical surface 614 thereof. At least at the surface 614, the scent agent may evaporate to spread through the environment, generally both inside and outside the lighting device 100. When an air flow exists in the cooling duct 410, generated by heat which in turn is generated by circuitry 420 and lighting elements 422 in operation, the evaporation of the scent agent, in particular at the surface 614 of the scent agent diffuser portion 610b by an air flow through openings between ribs 618, as indicated by dashed arrow 616 in FIGS. 7 and 8, is increased. Also a heating of the scent agent 612 taken up in the scent agent diffuser portion 610b, through heat generated in the lighting device 100 may as such increase the evaporation of the scent agent from the surface 614 of the scent agent diffuser portion 610b. A combination of these two effects (air flow in the cooling duct 410, and heating of the scent agent in the scent agent diffuser 610) will provide a distinct stronger scent distribution by the lighting device 100 in operation than in case the lighting device 100 is out of operation.

Figure 9:
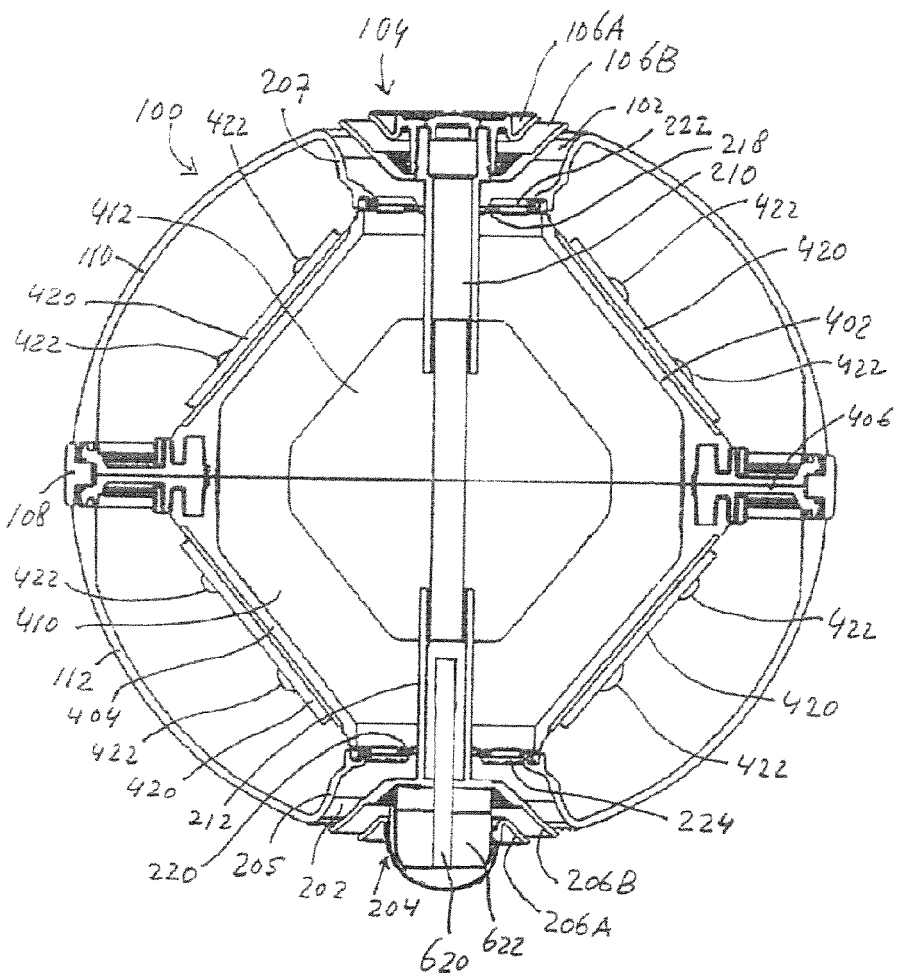
FIG. 9 depicts a cross-sectional view of a further embodiment of a lighting device according to the present invention, including a scent agent diffuser.
Figure 10:
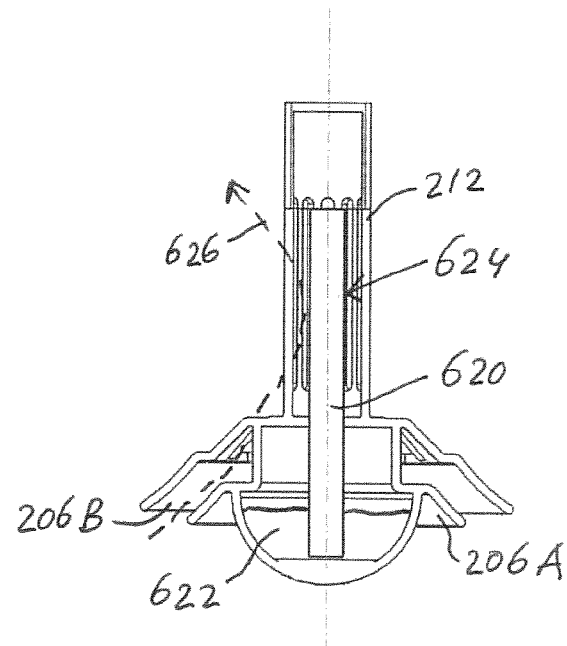
FIG. 10 depicts a cross-sectional view of a scent agent diffuser of the embodiment of the lighting device of FIG. 9.
Figure 11:
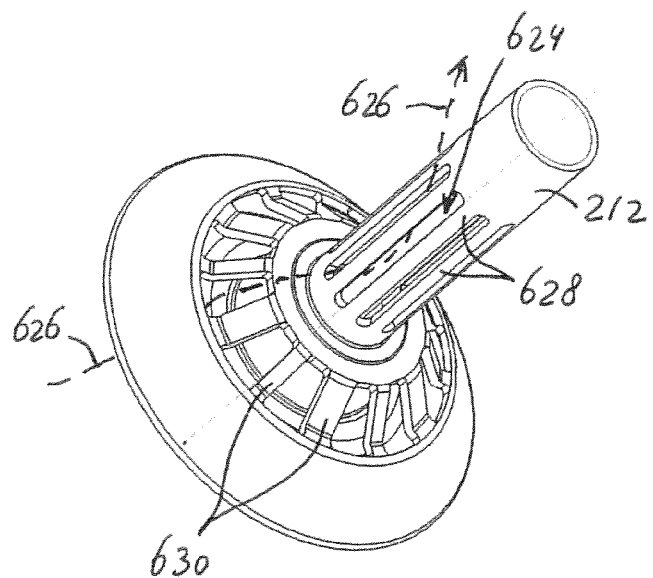
FIG. 11 depicts a perspective view of the scent agent diffuser of FIG. 10.

FIGS. 9, 10 and 11 depict a scent agent diffuser 620 configured to be accommodated in an embodiment of the lighting device 100 as illustrated by FIG. 4. In particular, FIG. 9 illustrates the scent agent diffuser 620 being mounted at the bottom of the lighting device 100. As shown more in detail in FIG. 10, the scent agent diffuser 620 comprises a body having an elongated, cylindrical body having a lower portion contacting a liquid or gel 622 carrying a scent agent. The liquid or gel 622 is taken up by the scent agent diffuser 620 material, which may be sponge-like or similar, such that at least the scent agent spreads throughout the scent agent diffuser 620, and is available at the cylindrical surface 624 thereof. At least at the surface 624, the scent agent may evaporate to spread through the environment, generally both inside and outside the lighting device 100. When an air flow exists in the cooling duct 410, generated by heat which in turn is generated by circuitry 420 and lighting elements 422 in operation, the evaporation of the scent agent, in particular at the surface 624 of the scent agent diffuser 620 by an air flow through openings between ribs 628 and 630, as indicated by dashed arrow 626 in FIGS. 10 and 11, is increased. Also a heating of the scent agent 622 taken up in the scent agent diffuser 520, through heat generated in the lighting device 100 may as such increase the evaporation of the scent agent from the surface 624 of the scent agent diffuser 620. A combination of these two effects (air flow in the cooling duct 410, and heating of the scent agent in the scent agent diffuser 620) will provide a distinct stronger scent distribution by the lighting device 100 in operation than in case the lighting device 100 is out of operation.

Figure 12:
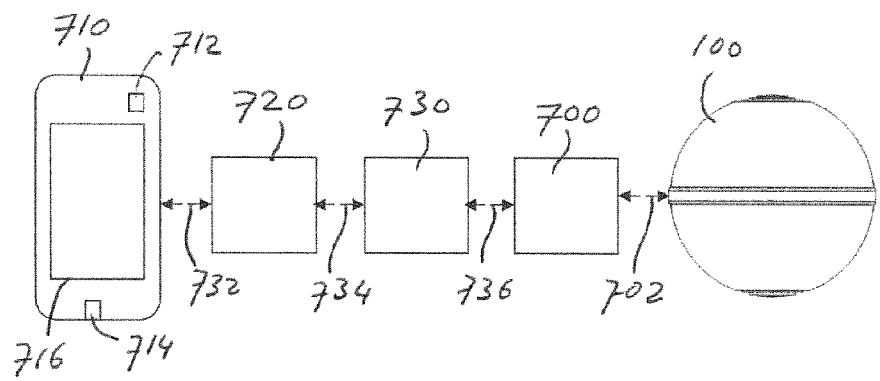
FIG. 12 depicts a diagram of an embodiment of a lighting system according to the present invention.
Figure 13:
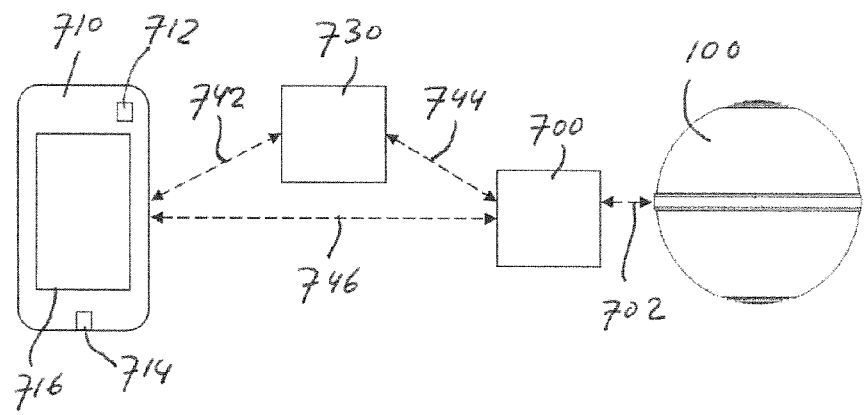
FIG. 13 depicts a diagram of another embodiment of a lighting system according to the present invention.

FIGS. 12 and 13 shows diagrams illustrating different embodiments of a system for controlling the color and/or intensity of the light emitted by the lighting device 100, e.g. emitted by an upper half and/or a lower half of the sphere-shaped lighting device 100.

Each lighting device 100 is connected, as indicated by a double dashed arrow 702, to a corresponding control unit 700 for communication of control signals from the control unit 700 to the lighting device 100, the control signals setting a predetermined color and/or intensity of light emitted by the lighting elements 422. In return, the lighting device 100 may communicate status signals to the control unit 700, the status signals being e.g. indicative of a temperature of the lighting elements, a status of the electrical circuitry 420 (if present), and/or an orientation of the lighting device 100 (see also below with reference to FIG. 17). The control unit 700 may be, may comprise, may be included in, or may be connected to the electrical circuitry 420, or may be separate therefrom. The control unit 700 may be included in the lighting device 100, or may be separate therefrom. The (control signal and/or status signal) connection between the control unit 700 and the lighting device 100 may be wired or wireless.

As illustrated in FIG. 12, in an embodiment, a user device 710 is connected (as indicated by double dashed arrow 732) to a network 720, such as the Internet. A router 730 also is connected (as indicated by double dashed arrow 734) to the network 720. The control unit 700 is connected (as indicated by double dashed arrow 736) to the router 730. In another embodiment, the user device 710 is connected to the router 730, whereas the control unit 700 is also connected to the router 730, as illustrated in FIG. 13 by double dashed arrows 742, 744, respectively. Alternatively or additionally, as further illustrated in FIG. 13 by double dashed arrow 746, the user device 710 is directly connected to the control unit 700.

The connections 732, 734, 736, 742, 744 and 746 serve to transmit control signals carrying control data from the user device 710 to the lighting device 100, and/or to transmit status signals carrying status data from the lighting device 100 to an application program, which may be running on the user device 710. The connections 732, 734, 736, 742, 744 and 746 may each be wired or wireless.

The user device 710 may comprise a computer, such as a PC or a laptop or a tablet computer, a PDA, a smartphone or similar device. The user device 710 may comprise a keyboard either having mechanically operable keys generating electrical signals, or it may comprise a touch detection device such as a touch screen having a keyboard function, i.e. allowing characters, control characters and symbols to be input. The user device 710 may also comprise a mouse device which may be any pointing device to select a position on a display and/or activate an application function through a user manipulation. Such application function activation may also be accomplished by manipulating a touchscreen of a touch-screen device, as explained in more detail below. The user device 710 may comprise other user action detection devices, for example an acceleration sensor 712 and/or a microphone 714, both being only schematically indicated. Accordingly, the lighting device 100 may be controlled by a user manipulating the user device 710 to generate signals carrying control data to be transmitted to the lighting device 100 as illustrated above with reference to FIGS. 12 and 13.

In an embodiment, the user device 710 is a smartphone or other portable computer comprising a touch screen 716. The user device 710 comprises an application (computer) program comprising program instructions which, when loaded in a processor of the user device 710, cause the user device to generate control signals carrying control data, the control signals being transmitted to the control unit 700 of the lighting device 100 using one of the communication paths indicated above with reference to FIGS. 12 and 13. Alternatively, the application program may be run on a remote computer, such as a server, available in the network 720, the user device 710 providing input data for the application program.

Examples of commands which may be executed by providing predetermined control signals, are: (1) every lighting device 100 in a particular router (wifi) network is provided with the same light setting as the latest light setting of an individual lighting device 100, (2) when a lighting device 100 has different predetermined stored light settings associated with it, a subsequent one of these light settings is selected, (3) a previously stored light setting is selected, (4) dimming of (part of) the lighting device 100, or (5) light setting of (part of) the lighting device 100.

Any of commands (1)-(3) above may e.g. be activated by shaking the user device 710, and thereby activating the acceleration sensor 712, resulting in the application program generating a control signal to execute the command. Command (4) above may e.g. be activated by blowing at the microphone 714, resulting in a noise being picked up by the microphone 714 and generation of a control signal to dim (a part of) the lighting device 710. Command (5) may e.g. be activated by submitting predetermined speech to the microphone 714, resulting in this speech being picked up by the microphone 714 and converted into a corresponding control signal to the lighting device 710.

As illustrated in FIGS. 14, 15 and 16, the application program may display different visual elements or items on the touch screen 716, which items may be manipulated by a user by touching the touch screen 716 within or near the border lines of the items.

FIG. 14 depicts a touch screen 716 displaying a title area 800 which may show a text explaining a particular function of the lighting device 100 to be controlled. For example, in FIG. 14 the title area 800 may display the word "COLOR". The touch screen 716 further shows a ring 802 and a circle 804, where the application is programmed to allow the circle 802 to be moved by a user touching the touch screen 716 at the location of the circle 804, along the ring 802. Each different position of the circle 804 along the ring 802 provides a different color value to the application. The touch screen 716 further shows an upper half circle 806 and a lower half circle 808. When a user touches the upper half circle 806, and thereafter positions the circle 804 along the ring 802, the upper half of the lighting device 100 will be controlled to emit light having the color as represented by the color value selected by positioning the circle 804 along the ring 802. Similarly, the color of the light emitted by the lower half of the lighting device 100 may be controlled by the user by touching the lower half circle 808, and thereafter positioning the circle 804 along the ring 802.

FIG. 15 depicts a touch screen 716 having a title area 800 which may show the word "SATURATION". The touch screen 716 further shows a ring segment 812 and a circle 814, where the application is programmed to allow the circle 814 to be moved by a user touching the touch screen 716 at the location of the circle 814, along the ring segment 812. Each different position of the circle 814 along the ring segment 812 provides a different saturation value to the application, where the left end of the ring segment 812 may represent the highest saturation value, the right end of the ring segment 812 may represent the lowest saturation value, and the path of the ring segment 812 between the left end and the right end represents decreasing saturation values when moving the circle 814 from the left end to the right end of the ring segment 812. The touch screen 716 further shows an upper half circle 816 and a lower half circle 818. When a user touches the upper half circle 816, and thereafter positions the circle 814 along the ring segment 812, the upper half of the lighting device 100 will be controlled to emit light having the saturation as represented by the saturation value selected by positioning the circle 814 along the ring segment 812. Similarly, the saturation of the light emitted by the lower half of the lighting device 100 may be controlled by the user by touching the lower half circle 818, and thereafter positioning the circle 814 along the ring segment 812.

FIG. 16 depicts a touch screen 716 having a title area 800 which may show the word "DIMMER". The touch screen 716 further shows a ring segment 822 and a circle 824, where the application is programmed to allow the circle 824 to be moved by a user touching the touch screen 716 at the location of the circle 824, along the ring segment 822. Each different position of the circle 824 along the ring segment 822 provides a different dimming value to the application, where the left end of the ring segment 822 may represent the highest light intensity value, the right end of the ring segment 822 may represent the lowest light intensity value, and the path of the ring segment 822 between the left end and the right end represents decreasing light intensity values when moving the circle 824 from the left end to the right end of the ring segment 822. The touch screen 716 further shows an upper half circle 826 and a lower half circle 828. When a user touches the upper half circle 826, and thereafter positions the circle 824 along the ring segment 822, the upper half of the lighting device 100 will be controlled to emit dimmed light as represented by the dimming value selected by positioning the circle 824 along the ring segment 822. Similarly, the dimming of the light emitted by the lower half of the lighting device 100 may be controlled by the user by touching the lower half circle 828, and thereafter positioning the circle 824 along the ring segment 822. A further circle 830 may provide an indication of the actual dimming status.

The lighting device 100 may provide status data to the control unit 700. The control unit 700 in turn may transfer the status data to the application program. Status data may e.g. comprise temperature data provided by one or more temperature sensors in the lighting device 100. In turn, the application program may control the lighting device 100 by setting a dimming range of the lighting device 100 appropriate for the temperature(s) as sensed in the lighting device 100. For example, if a high temperature is sensed, the lighting device 100 may be dimmed to a level to decrease the temperature and disabling higher dimming levels, or may even be switched off.

Figure 17:
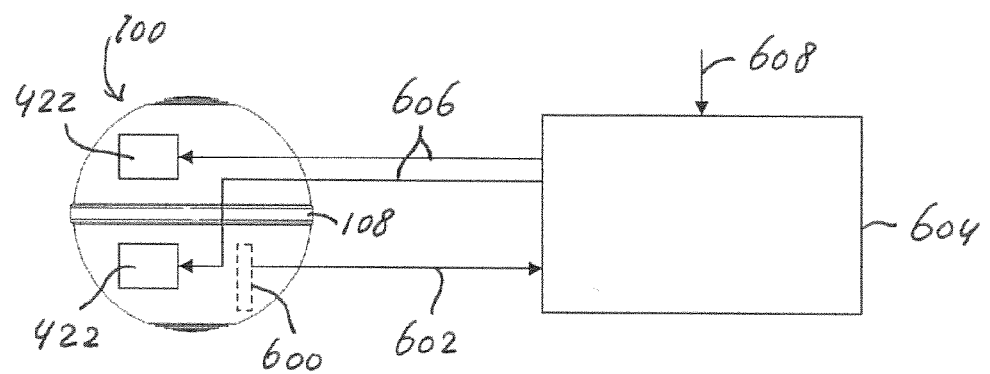
FIG. 17 depicts a diagram of a further embodiment of a lighting system according to the present invention.

FIG. 17 illustrates the lighting device 100 comprising an orientation sensor 600 for sensing an orientation of the lighting device 100. The orientation sensor is configured to output an orientation signal 602 to a control module 604, which may be the same as, or be part of the control unit 700 described above. The control module 604 is adapted for receiving the orientation signal 602, and for controlling at least one of the lighting elements 422 depending on the orientation sensed by the orientation sensor 600. The control module 604 may control electric power 606 supplied to each of the lighting elements 422 from a power supply 608, such as a mains power supply. In an embodiment, the upper half of the lighting device 100 emits light having a first intensity and a first color, while the lower half of the lighting device 100 emits light having a second intensity and a second color. The fact which half of the lighting device 100 is to be considered as the upper half and which half is to be considered as the lower half, is determined by the orientation sensor 600. When the lighting device 100 is put upside-down thereafter, the previous upper half becomes the lower half, and the previous lower half becomes the upper half. This is detected by the orientation sensor 600, and the control module 604 may adapt the electric power to each of the lighting elements 422 such that again the upper half of the lighting device 100 emits light having the first intensity and the first color, while the lower half of the lighting device 100 emits light having the second intensity and the second color. The control module 604 may be implemented in hardware or in software.

As explained above by reference to several embodiments, the present invention relates to a lighting device with a support structure having lighting elements arranged thereon. The support structure has an internal cooling duct having a duct wall. At least a part of duct wall is in thermal contact with the lighting elements. The cooling duct is configured to allow a natural air flow absorbing heat generated by the lighting elements from the duct wall. The cooling duct extends through the support structure from a first opening having a first cross-sectional area to a second opening having a second cross-sectional area. The cooling duct contains a filler body having a substantially bi-conical shape. The filler body and the duct wall form a cooling duct portion with a third cross-sectional area greater than the first cross-sectional area and/or the second cross-sectional area. The lighting device is part of a lighting system. The system comprises a control unit coupled to the lighting device. The control unit is configured to receive control data and to cause the lighting device to operate based on the control data. The system further comprises a user device configured to generate input to an application program configured to generate the control data based on the input, and to transmit the control data to the control unit.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The term coupled, as used herein, is defined as connected, although not necessarily directly.

A single processor or other unit may fulfil the functions of several items recited in the claims.

The terms (computer) program, software application, and the like as used herein, are defined as a sequence of instructions designed for execution on a computer system. A program, computer program, or software application may include a subroutine, a function, a procedure, an object method, an object implementation, an executable application, an applet, a servlet, a source code, an object code, a shared library/dynamic load library and/or other sequence of instructions designed for execution on a computer system.

A computer program may be stored and/or distributed on a suitable medium, such as an optical storage medium or a solid-state medium supplied together with or as part of other hardware, but also be distributed in other forms, such as via the Internet or other wired or wireless telecommunication systems.

The invention claimed is:

1. A lighting device comprising a support structure having lighting elements arranged thereon, the support structure comprising an internal cooling duct having a duct wall, at least a part of duct wall being in thermal contact with the lighting elements, the cooling duct configured to allow a natural air flow absorbing heat generated by the lighting elements from the duct wall, the cooling duct extending through the support structure from a first opening having a first cross-sectional area to a second opening having a second cross-sectional area, wherein the cooling duct contains a filler body, the filler body and the cooling duct forming a cooling duct portion having a third cross-sectional area larger than the first cross-sectional area and/or the second cross-sectional area, wherein the filler body has a substantially bi-conical shape.

2. The lighting device of claim 1, wherein at least a part of the duct wall opposite the filler body is in thermal contact with the lighting elements.

3. The lighting device of claim 1, wherein the filler body is arranged centrally in the cooling duct.

4. The lighting device of claim 1, wherein, in use of the lighting device, the second opening is at a higher vertical level than the first opening.

5. The lighting device of claim 1, wherein, in use of the lighting device, the first opening is at a bottom side of the support structure.

6. The lighting device of claim 1, wherein, in use of the lighting device, the second opening is at a top side of the support structure.

7. The lighting device of claim 1, wherein the cooling duct comprises two substantially frusto-conical parts having bases connected to one another.

8. The lighting device of claim 7, wherein the lighting elements are mounted on an outer surface of the frusto-conical parts.

9. The lighting device of claim 7 or 8, wherein the frusto-conical parts are multi-faceted to define mounting planes for the lighting elements.

10. The lighting device of claim 1, wherein the lighting elements comprise light emitting diodes, LEDs.

11. The lighting device of claim 1, wherein the support structure comprises a light-transmitting sphere-shaped enclosure.

12. The lighting device of claim 1, comprising a scent agent diffuser arranged in the cooling duct or arranged to be in the air flow downstream of the cooling duct.

13. The lighting device of claim 12, wherein the scent agent diffuser has a surface arranged to be in contact with the air flow.

14. The lighting device of claim 1, comprising a rotor configured to be driven by the air flow.

15. A lighting system comprising:
a lighting device comprising a support structure having lighting elements arranged thereon, the support structure comprising an internal cooling duct having a duct wall, at least a part of duct wall being in thermal contact with the lighting elements, the cooling duct configured to allow a natural air flow absorbing heat generated by the lighting elements from the duct wall, the cooling duct extending through the support structure from a first opening having a first cross-sectional area to a second opening having a second cross-sectional area, wherein the cooling duct contains a filler body, the filler body and the cooling duct forming a cooling duct portion having a third cross-sectional area larger than the first cross-sectional area and/or the second cross-sectional area, wherein the filler body has a substantially bi-conical shape, the lighting system further comprising:
a control unit coupled to the lighting device, the control unit being configured to receive control data and to cause the lighting device to operate based on the control data; and a user device configured to generate input to an application program, the application program being configured to generate the control data based on the input, and to transmit the control data to the control unit, wherein the control unit further is configured to receive status data from the lighting device, and to transmit the status data to the application program.

16. The lighting system of claim 15, wherein the transmission of the control data or the status data is through a network, such as the Internet or a local network.

17. The lighting system of claim 15, wherein the user device comprises a touch screen, and the input to the application program is generated by the user manipulating the touch screen.

18. The lighting system of claim 15, wherein the user device comprises an acceleration sensor, and the input to the application program is generated by the user moving, in particular shaking, the user device.

19. The lighting system of claim 15, wherein the user device comprises a microphone, and the input to the application program is generated by the user providing a sound or speech to the microphone.

20. The lighting system of claim 15, further comprising:
an orientation sensor for sensing an orientation of the lighting device, the orientation sensor configured to output an orientation signal;
a control module for receiving the orientation signal, and for controlling at least one of the lighting elements depending on the orientation sensed by the orientation sensor.

* * * * *